(12) United States Patent
Schimperna et al.

(10) Patent No.: US 9,353,125 B2
(45) Date of Patent: May 31, 2016

(54) PROCESS FOR THE PREPARATION OF BENZOHETERO [1,3]-DIAZOLE COMPOUNDS DISUBSTITUTED WITH HETEROARYL GROUPS

(75) Inventors: Giuliana Schimperna, Novara (IT); Gabriele Bianchi, Novara (IT)

(73) Assignee: ENI S.P.A. (IT)

( * ) Notice: Subject to any disclaimer, the term of this patent is extended or adjusted under 35 U.S.C. 154(b) by 0 days.

(21) Appl. No.: 14/237,538

(22) PCT Filed: Aug. 1, 2012

(86) PCT No.: PCT/IB2012/053927
§ 371 (c)(1),
(2), (4) Date: Mar. 18, 2014

(87) PCT Pub. No.: WO2013/021315
PCT Pub. Date: Feb. 14, 2013

(65) Prior Publication Data
US 2014/0221663 A1    Aug. 7, 2014

(30) Foreign Application Priority Data

Aug. 8, 2011  (IT) ............................. MI2011A1516

(51) Int. Cl.
| | |
|---|---|
| *C07D 495/04* | (2006.01) |
| *C07D 413/14* | (2006.01) |
| *C07D 417/14* | (2006.01) |
| *C07D 409/14* | (2006.01) |
| *C07D 519/00* | (2006.01) |

(52) U.S. Cl.
CPC ............ *C07D 495/04* (2013.01); *C07D 409/14* (2013.01); *C07D 413/14* (2013.01); *C07D 417/14* (2013.01); *C07D 519/00* (2013.01)

(58) Field of Classification Search
None
See application file for complete search history.

(56) References Cited

PUBLICATIONS

Zhou, Huaxing, et al., "Donor-Acceptor Polymers Incorporating Alkylated Dithienylbenzothiadiazole for Bulk Heterojunction Solar Cells: Pronounced Effect of Positioning Alkyl Chains", Macromolecules, American Chemical Society, Washington D.C., vol. 43, No. 2, Feb. 26, 2010, pp. 811-820.
Li, J.C., et al., "Synthesis of a benzothiadiazole/thiophene-based oligomer for bulk heterojunction photovoltaic cells", Synthetic Materials, Elsevier Sequoia, Lausanne, CH., vol. 159, No. 3-4, Feb. 1, 2009, pp. 201-208.
Kitamura, Chitoshi, et al., "Design of Narrow-Bandgap Polymers. Syntheses and Properties of Monomers and Polymers Containing Aromatic-Donor and o-Quinoid-Acceptor Units", Chemistry of Materials, American Chemical Society, Washington D.C., vol. 8, No. 2, Jan. 1, 1996, pp. 570-578.
Kim, et al., "A polymer gel electrolyte to achieve ≥6% power conversion efficiency with a novel organic dye incorporating a low-bandgap chromophore", J. Mater. Chem., vol. 18, 2008, pp. 5223-5229.
Tamba, et al., "Palladium-Catalyzed C—H Functionalization of Heteroarenes with Aryl Bromides and Chlorides", J. Org. Chem., vol. 75, 2010, pp. 6998-7001.
Steinberger, et al., "A-D-A-D-A-Type Oligothiophenes for Vacuum-Deposited Organic Solar Cells", Organic Letter, vol. 13, No. 1, Jan. 7, 2011, pp. 90-93.
Price, et al., "Fluorine substituted conjugated polymer of medium band gap yields 7% efficiency in polymer-fullerene solar cells", J. Am. Chem. Soc., vol. 133, Mar. 30, 2011, pp. 4625-4631.

*Primary Examiner* — Kamal Saeed
(74) *Attorney, Agent, or Firm* — Tarolli, Sundheim, Covell & Tummino LLP

(57) ABSTRACT

Process for the preparation of a benzohetero[1,3]diazole compound disubstituted with heteroaryl groups which comprises reacting at least one benzohetero[1,3]diazole compound disubstituted with at least one heteroaryl compound. Said benzohetero[1,3]diazole compound disubstituted with heteroaryl groups can be advantageously used in the construction of luminescent solar concentrators (LSC). Furthermore, said benzohetero[1,3]diazole compound disubstituted with heteroaryl groups can be advantageously used in the construction of photovoltaic devices such as, for example, photovoltaic cells, photovoltaic modules, solar cells, solar modules, on both a rigid and flexible support. Said benzohetero[1,3]diazole compound disubstituted with heteroaryl groups can also be advantageously used as a precursor of monomeric units in the preparation of semiconductor polymers.

24 Claims, No Drawings

PROCESS FOR THE PREPARATION OF BENZOHETERO [1,3]-DIAZOLE COMPOUNDS DISUBSTITUTED WITH HETEROARYL GROUPS

The present invention relates to a process for the preparation of a benzohetero[1,3]diazole compound disubstituted with heteroaryl groups.

More specifically, the present invention relates to a process for the preparation of a benzohetero[1,3]diazole compound disubstituted with heteroaryl groups which comprises reacting at least one disubstituted benzohetero[1,3]diazole compound with at least one heteroaryl compound.

Said benzohetero[1,3]diazole compound disubstituted with heteroaryl groups can be advantageously used in the construction of luminescent solar concentrators (LSC). Furthermore, said benzohetero[1,3]diazole compound disubstituted with heteroaryl groups can be advantageously used in the construction of photovoltaic devices such as, for example, photovoltaic cells, photovoltaic modules, solar cells, solar modules, on both a rigid and flexible support. Said benzohetero[1,3]diazole compound disubstituted with heteroaryl groups can also be advantageously used as a precursor of monomeric units in the preparation of semiconductor polymers.

It is known that neither polymer or silicon photovoltaic cells are capable of efficiently exploiting all the solar radiation. Their efficiency, in fact, is maximum only within a certain spectrum range which comprises a part of visible radiation and a part of infrared radiation.

Spectrum convertor materials which capture solar radiation outside the optimal spectral range and convert it to effective radiation, can be used for enhancing the performance of photovoltaic cells. Furthermore, luminescent solar concentrators can be produced with these materials, which allow a further increase in the production of current in photovoltaic cells.

Said luminescent solar concentrators generally consist of large sheets of material transparent to solar radiation, in which fluorescent substances are dispersed, which act as spectrum converters. Due to the effect of the optical phenomenon of total reflection, the radiation emitted by the fluorescent molecules is "guided" towards the thin edges of the sheet where it is concentrated on photovoltaic cells or solar cells positioned therein. In this way, large surfaces of low-cost materials (photoluminescent sheets) can be used for concentrating the light on small surfaces of high-cost materials (photovoltaic cells or solar cells).

It is known that some benzothiadiazole compounds, in particular 4,7-di-2-thienyl-2,1,3-benzothia-diazole (DTB), are fluorescent compounds which can be used as spectrum convertor materials in luminescent solar concentrators. Materials of this type are described in Italian patent application MI 2009 A 001796 in the name of the Applicant.

4,7-di-2-thienyl-2,1,3-benzothiadiazole (DTB) is also used for the synthesis of electron-donor polymers used in the construction of photovoltaic devices such as solar cells as described, for example, in "Organic Photovoltaics: Mechanism, Materials and Devices" (2005), Wiley Ed., Chapter 17.

4,7-di-2-thienyl-2,1,3-benzothiadiazole (DTB) is a compound of great interest, whose synthesis is currently the subject of numerous research studies.

4,7-di-2-thienyl-2,1,3-benzothiadiazole (DTB) is generally prepared by means of a Stille reaction, by reacting 4,7-dibromo-2,1,3-benzothiadiazole and an excess of tri-n-butyl(thien-2-yl)stannane. Said reaction is generally carried out in the presence of catalysts containing palladium, at temperatures ranging from 60° C. to 145° C., in the presence of solvents such as, for example, toluene, xylene, 1,2-dimethoxyethane, tetrahydrofuran, dimethylsulfoxide, N,N-dimethylformamide, for a time ranging from 35 minutes to 18 hours. The yields normally range from 70% to 98%.

According to what is described by Kitamura et al. in "Chemistry of Material" (1996), Vol. 8, pages 570-578, for example, 4,7-di-2-thienyl-2,1,3-benzothia-diazole (DTB) can be prepared by reacting 4,7-dibromo-2,1,3-benzothiadiazole and tri-n-butyl(thien-2-yl)stannane, in the presence of tetrahydrofuran, at 66° C., for 3 hours. Bis(triphenylphosphine)palladium-(II)chloride [$PdCl_2(PPh_3)_2$] is used as catalyst, in a quantity equal to 2 moles per 100 moles of 4,7-dibromo-2,1,3-benzothiadiazole. At the end of the reaction, the solvent is removed by evaporation at reduced pressure and the residue obtained is purified by elution on a silica gel chromatographic column using a mixture of methylene chloride/hexane (1/1 vol/vol) as eluent, obtaining 4,7-di-2-thienyl-2,1,3-benzothiadiazole (DTB) with a yield equal to 82%.

An analogous process is described by Kim et al. in "Journal of Material Chemistry" (2008), Vol. 18, pages 5223-5229, in which 4,7-di-2-thienyl-2,1,3-benzothia-diazole (DTB) can be prepared by reacting 4,7-dibromo -2,1,3-benzothiadiazole and tri-n-butyl(thien-2-yl)stannane, in the presence of tetrahydrofuran, at 66° C., for 3 hours. Bis(triphenylphosphine) palladium-(II)chloride [$PdCl_2(PPh_3)_2$] is used as catalyst. Also in this case, at the end of the reaction, the solvent is removed by evaporation at reduced pressure and the residue obtained is purified by elution on a silica gel chromatographic column using a mixture of methylene chloride/hexane (1/1 vol/vol) as eluent, obtaining 4,7-di-2-thienyl-2,1,3-benzothiadiazole (DTB) with a yield equal to 88%.

Although the above processes allow 4,7-di-2-thienyl-2,1, 3-benzothia-diazole (DTB) to be obtained with good yields, they can have some disadvantages. In particular:

in order to be completed, the reactions require relatively long times, ranging from a few hours to tens of hours (normally from 3 hours to 72 hours) and an excess of tri-n-butyl(thien-2-yl)stannane, with consequent higher production costs and disposal costs of the waste products;

the quantities of catalyst are relatively high: 2 moles of palladium per 100 moles of 4,7-dibromo-2,1,3-benzothiadiazole are normally used and, in any case, never less than 0.5 moles per 100 moles of dibromo-derivative (although the quantities, in absolute terms, are small, they are in any case high considering the cost of palladium or, as it is not always possible to prepare its complexes in situ, of its complexes);

in some cases, the use of the solvents proposed creates problems relating to their toxicity, from both an environmental point of view and also with respect to the health of the operators, in addition to problems relating to their disposal which is often costly.

Efforts have in fact been made in the art to overcome the above drawbacks.

Italian patent application MI 2010 A0001316, for example, in the name of the Applicant, describes a process for the preparation of benzothiadiazole compounds, in particular 4,7-di-2-thienyl-2,1,3-benzothiadiazole (DTB), which comprises reacting a derivative of 2,1,3-benzothiadiazole, in particular 4,7-dibromo-2,1,3-benzothiadiazole, with a stoichiometric quantity of a tri-n-alkyl(thien-2-yl)stannane, in particular tri-n-butyl(thien-2-yl)stannane, in the presence of a solvent selected from dimethylsulfoxide (DMSO) and dimethylformamide (DMF) and of a catalyst containing palladium (Pd), at a temperature higher than 110° C., preferably ranging from 120° C. to 160° C. Said catalyst containing palladium can be selected from palladium complexes in oxidation state (0) or (II), such as, for example, bis (triphenylphosphine)palladium(II) chloride [Pd (PPh$_3$)$_2$Cl$_2$], bis (triphenylphosphine)palladium(II) acetate [Pd(PPh$_3$)$_2$(OAc)$_2$], tetrakis(triphenylphosphine) -palladium(0) [Pd (PPh$_3$)$_4$], bis(dibenzylidene)palladium(0) [Pd(dba)$_2$ wherein dba=C$_6$H$_5$CH═CHCOCH═CHC$_6$H$_5$], bis(acetonitrile)palladium(II) chloride [Pd(CH$_3$CN)$_2$Cl$_2$], benzyl[bis(triphenylphosphine)]palladium(II) chloride [C$_6$H$_5$CH$_2$Pd(PPh$_3$)$_2$Cl]. The palladium complex can also be prepared in situ, operating according to the known techniques, by adding a palladium salt to the reaction mixture together with the appropriate ligand dissolved in the reaction solvent. The above process is said to be capable of providing high yields (98%) of derivatives of 2,1,3-benzothiadiazole, in particular 4,7-di-2-thienyl-2,1,3-benzothiadiazole (DTB), also operating with lower quantities of catalyst, with short reaction times (time less than one hour) and in stoichiometric ratios.

Even if the above process for the preparation of 4,7-di-2-thienyl-2,1,3-benzothiadiazole (DTB) allows the desired product to be obtained with high yields (98%) and in a short time (time less than one hour), it has a great disadvantage linked to the use of derivatives of tin.

Tri-n-butyl(thien-2-yl)stannane, a commercial product, is prepared starting from thiophene and tri-n-butylstannyl chloride. The reaction takes place through a two-step process which comprises the formation of 2-thienyl-lithium starting from thiophene and an alkyl-lithium derivative and the subsequent treatment of 2-thienyl-lithium in situ with tri-n-butylstannyl chloride. Alkyl-lithium derivatives are highly flammable substances which must be carefully handled in the complete absence of oxygen and humidity. Another important problem linked to the use of tin derivatives lies in their toxicity and in the damage that they can cause to both the environment and to the health of the operators.

As already reported above, the process for the preparation of 4,7-di-2-thienyl-2,1,3-benzothiadiazole (DTB) (Ia) comprises reacting 4,7-dibromo-2,1,3-benzothiadiazole (IIa) with tri-n-butyl(thien-2-yl)stannane (IIIa), as reported in the following scheme:

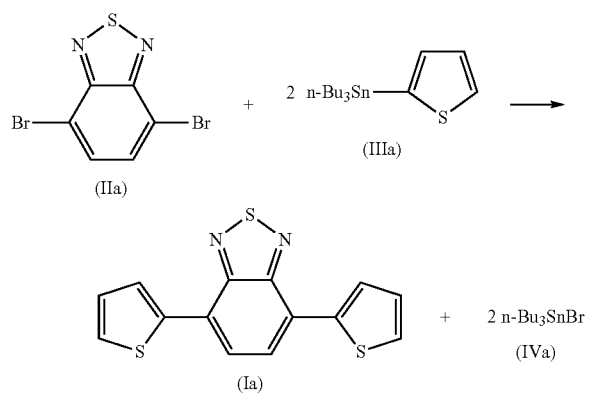

using the operative conditions specified above.

In addition to the problems reported above linked to the use of tri-n-butyl(thien-2-yl)stannane (IIa), there are also problems relating to the disposal of processing waste-products. As can be seen from the above scheme, in fact, for each mole of 4,7-di-2-thienyl-2,1,3-benzothiadiazole (DTB) (Ia) obtained, two moles of tri-n-butylstannyl bromide (IVa) are formed, which must be appropriately disposed of with a consequent increase in the process costs.

Systems are described in literature for forming aryl-aryl (Ar—Ar) bonds without the use of derivatives of tin. Said reactions, known as direct arylations of aromatic systems, are generally carried out by reacting an aryl halide (Ib) with an aryl or heteroaryl compound (IIb), as reported in the following scheme:

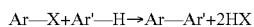

(Ib) (IIb)

wherein X represents a chlorine, bromine or iodine atom, in the presence of a catalyst containing palladium and, in some cases, in the presence of phosphines as palladium ligands.

Tamba et al. in "Journal of Organic Chemistry" (2010), Vol. 75, pages 6998-7001, for example, describe an arylation reaction according to the scheme reported above, wherein Ar' is a benzothiophene, in the presence of a catalyst containing palladium such as, for example, bis(tri-t-butylphosphine)palladium(II) [Pd(Pt-tBu$_3$)$_2$], of a solvent such as, for example, dimethylformamide (DMF) and of a strong base such as, for example, lithium t-butylate (LiO-t-Bu), at a temperature of 100° C., for 15 hours.

Roger et al. in "Green Chemistry" (2009), Vol. 11, pages 425-432, describe an arylation reaction according to the scheme reported above, wherein Ar' is a thiophene substituted in position 2, in the presence of a catalyst containing palladium such as, for example, palladium(II)acetate ([Pd (OAc)$_2$]), of a solvent such as, for example, dimethylacetamide (DMAc) and of a base such as, for example potassium acetate (KOAc), at a temperature of 150° C., for 20 hours.

Chen et al. in "Chemical Communication" (2010), doi: 10.1039/C0CC04302H, describe an arylation reaction according to the scheme reported above, wherein Ar' is a thiophene substituted in position 2 with a group (R)$_3$Si wherein R can be an alkyl group (e.g., a methyl group), in the presence of a catalyst containing palladium such as, for example, palladium(II)acetate ([Pd(OAc)$_2$]) associated with diphenylphosphinobutane (DPPB) as ligand, of a solvent such as, for example, dimethylacetamide (DMAc) and of a base such as, for example potassium acetate (KOAc), at a temperature of 120° C., for a time ranging from 1 hour to 48 hours.

The processes reported above, however, have various critical points such as, for example:

the use of aryl or heteroaryl compounds, in particular thiophenes, substituted in position 2, and, consequently, the necessity of subjecting the end-product to further treatments (e.g., deprotonation) in order to obtain the desired product, and the impossibility of using the product obtained as precursor of monomeric units in the preparation of semiconductor polymers;

the use of di- or tri-phenyl phosphines as palladium ligands and, consequently, as these compounds cannot always be prepared in situ, higher process costs and the necessity of subjecting the end-product to further treatments (e.g., purification) in order to eliminate the phosphinoxides formed as by-products during the reaction;

the use of strong bases [e.g., lithium t-butylate (LiO-t-Bu)] and, consequently, difficulty in handling said bases, a higher possibility of damage to both the environment and health of the operators, and higher disposal costs;

relatively lengthy temperature and reaction times and, consequently, energy costs and process time-lengthening that can cause degradation of the product obtained.

The Applicant has therefore considered the problem of finding a process for the preparation of a benzohetero[1,3]diazole compound disubstituted with heteroaryl groups, capable of overcoming the above drawbacks. In particular, the Applicant has considered the problem of finding a process for the preparation of a benzohetero[1,3]diazole compound disubstituted with heteroaryl groups, through the direct arylation, more specifically through a double direct arylation, of a benzohetero[1,3]diazole compound.

The Applicant has now found that the preparation of a benzohetero[1,3]diazole compound disubstituted with heteroaryl groups can be carried out by means of a process comprising a double direct arylation of a disubstituted benzohetero[1,3]diazole compound, more specifically by means of a process which comprises reacting at least one benzohetero[1,3]diazole compound disubstituted with at least one heteroaryl compound.

There are numerous advantages obtained by operating according to the above process such as, for example:
- the possibility of functionalizing the product obtained to be able to use it, for example, in polymerizations;
- direct use of the product obtained without the necessity of subjecting it to further treatments (e.g., purification) to eliminate by-products that can be formed during the reaction such as, for example, phosphineoxides;
- greater safety conditions (e.g., the absence of strong bases), for both the health of the operators and from an environmental point of view;
- relatively short temperature and reaction times, with lower energy costs and shorter process times thus avoiding the possible degradation of the product obtained.

Said benzohetero[1,3]diazole compound disubstituted with heteroaryl groups can be advantageously used in the construction of luminescent solar concentrators (LSCs). Furthermore said benzohetero[1,3]diazole compound disubstituted with heteroaryl groups can be advantageously used in the construction of photovoltaic devices such as, for example, photovoltaic cells, photovoltaic modules, solar cells, solar modules, on both a rigid and flexible support. Said benzohetero[1,3]diazole compound disubstituted with heteroaryl groups can also be advantageously used as a precursor of monomeric units in the preparation of semiconductor polymers.

An object of the present invention therefore relates to a process for the preparation of a benzohetero[1,3]diazole compound disubstituted with heteroaryl groups having general formula (I)

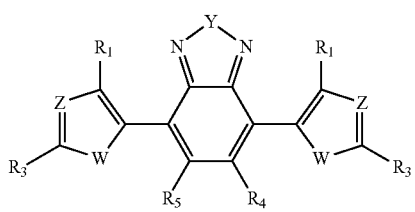

(I)

wherein:
W represents an oxygen atom; a sulfur atom; an NR group wherein R represents a hydrogen atom, or a linear or branched $C_1$-$C_{20}$, preferably $C_2$-$C_{10}$, alkyl group;
Y represents a sulfur atom; an oxygen atom; a selenium atom; an NR group wherein R represents a hydrogen atom, or a linear or branched $C_1$-$C_{33}$, preferably $C_6$-$C_{24}$, alkyl group;
Z represents a nitrogen atom; or a $CR_2$ group wherein $R_2$ has the meanings reported below;
$R_1$ represents a hydrogen atom; a linear or branched $C_1$-$C_{20}$, preferably $C_2$-$C_{10}$, alkyl group; a cycloalkyl group optionally substituted; an aryl group optionally substituted; a linear or branched $C_1$-$C_{20}$, preferably $C_2$-$C_{10}$, alkoxyl group; a polyethyleneoxyl group R—O—[—$CH_2$—$CH_2$—O]$_n$— wherein R has the same meaning reported above and n is an integer ranging from 1 to 4; a —R'—OH group wherein R' represents a linear or branched $C_1$-$C_{20}$, preferably $C_2$-$C_{10}$, alkylene group; a —R'—OR" group wherein R' has the same meanings reported above and R" represents a linear or branched $C_1$-$C_{20}$, preferably $C_2$-$C_{10}$, alkyl group, or a polyethyleneoxyl group R—O—[—$CH_2$—$CH_2$—O]$_n$— wherein R has the same meaning reported above and n is an integer ranging from 1 to 4; a —COR group wherein R has the same meanings reported above; a —COOR group wherein R has the same meanings reported above; a —CHO group; a cyano (—CN) group;
$R_3$ represents a hydrogen atom; a linear or branched $C_1$-$C_{20}$, preferably $C_2$-$C_{10}$, alkyl group; a cycloalkyl group optionally substituted; an aryl group optionally substituted; a heteroaryl group optionally substituted; a —CHO group; a —COR group wherein R has the same meanings reported above; a —COOR group wherein R has the same meanings reported above; a —CONR$_2$ group wherein $R_2$ has the same meanings reported below; a cyano (—CN) group;
$R_2$ represents a hydrogen atom; a linear or branched $C_1$-$C_{20}$, preferably $C_2$-$C_{10}$, alkyl group; or, when $R_3$ is different from hydrogen, or when $R_1$=$R_2$, $R_2$ represents a linear or branched $C_1$-$C_{20}$, preferably $C_2$-$C_{10}$, alkoxyl group;
or $R_1$ and $R_2$, can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as oxygen, sulfur, nitrogen, silicon, phosphorous, selenium;
or $R_2$ and $R_3$, can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as oxygen, sulfur, nitrogen, silicon, phosphorous, selenium;
$R_4$ and $R_5$, the same as each other, represent a hydrogen atom; a linear or branched $C_1$-$C_{20}$, preferably $C_2$-$C_{10}$, alkyl group; a linear or branched $C_1$-$C_{20}$, preferably $C_2$-$C_{10}$, alkoxyl group; a —COOR group wherein R has the same meanings reported above; a cyano (—CN) group;
or $R_4$ and $R_5$, can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as oxygen, sulfur, nitrogen, silicon, phosphorous, selenium;
said process comprising reacting at least one disubstituted benzohetero[1,3]diazole compound having general formula (II):

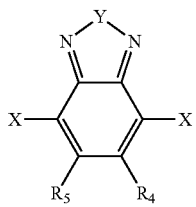

(II)

wherein X represents a halogen atom selected from chlorine, fluorine, bromine, iodine, preferably bromine; Y, $R_4$ and $R_5$, have the same meanings described above;
with at least one heteroaryl compound having general formula (III):

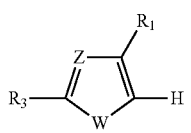

(III)

wherein W, Z, $R_1$ and $R_3$, have the same meanings described above.

For the purposes of the present description and of the following claims, the definitions of the numerical ranges always comprise the extremes unless otherwise specified.

The term "$C_1$-$C_{20}$ alkyl group" refers to a linear or branched alkyl group having from 1 to 20 carbon atoms. Specific examples of a $C_1$-$C_{20}$ alkyl group are: methyl, ethyl, n-propyl, iso-propyl, n-butyl, iso-butyl, t-butyl, pentyl, ethylhexyl, hexyl, heptyl, octyl, nonyl, decyl, dodecyl.

The term "$C_1$-$C_{20}$ alkylene group" refers to a linear or branched alkylene group having from 1 to 20 carbon atoms. Specific examples of a $C_1$-$C_{20}$ alkylene group are: methylene, ethylene, n-propylene, iso-propylene, n-butylene, iso-butylene, t-butylene, pentylene, ethyl-hexylene, hexylene, heptylene, octylene, nonylene, decylene, dodecylene The term "cycloalkyl group" refers to a cycloalkyl group having from 3 to 10 carbon atoms. Said cycloalkyl group can be optionally substituted with one or more groups, the same or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amino groups; nitro groups. Specific examples of a cycloalkyl group are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl.

The term "aryl group" refers to an aromatic carbocyclic group. Said aromatic carbocyclic group can be optionally substituted by one or more groups, the same or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups, cyano groups; amino groups; nitro groups. Specific examples of an aryl group are: phenyl, methylphenyl, trimethylphenyl, methoxyphenyl, hydroxyphenyl, phenyloxyphenyl, fluorophenyl, pentafluorophenyl, chlorophenyl, nitrophenyl, dimethylaminophenyl, naphthyl, phenylnaphthyl, phenanthrene, anthracene.

The term "$C_1$-$C_{20}$ alkoxyl group" refers to a linear or branched alkoxyl group having from 1 to 20 carbon atoms. Specific examples of a $C_1$-$C_{20}$ alkoxyl group are: methoxyl, ethoxyl, n-propoxyl, iso-propoxyl, n-butoxyl, iso-butoxyl, t-butoxyl, pentoxyl, hexyloxyl, heptyloxyl, octyloxyl, nonyloxyl, decyloxyl, dodecyloxyl.

The term "polyethyleneoxyl group" refers to a group having oxyethylene units in the molecule. Specific examples of a polyethyleneoxyl group are: methyloxy-ethyleneoxyl, methyloxy-diethyleneoxyl, 3-oxatetraoxyl, 3,6-dioxaheptyloxyl, 3,6,9-trioxadecyloxyl, 3,6,9,12-tetraoxahexadecyloxyl.

The term "heteroaryl group" means an aromatic heterocyclic group, penta- or hexa-atomic, also benzocondensed or heterobicyclic, containing from 1 to 4 heteroatoms selected from nitrogen, oxygen, sulfur, silicon, selenium, phosphorus. Said heteroaryl group can be optionally substituted by one or more groups, the same or different from each other, selected from: halogen atoms such as, for example, fluorine, chlorine, preferably fluorine; hydroxyl groups; $C_1$-$C_{20}$ alkyl groups, $C_1$-$C_{20}$ alkoxyl groups; cyano groups; amino groups; nitro groups. Specific examples of a heteroaryl group are: pyridine, methylpyridine, methoxypyridine, phenylpyridine, fluoropyridine, pyrimidine, pyridazine, pyrazine, triazine, tetrazine, quinoline, quinoxaline, quinazoline, furan, thiophene, hexylthiophene, pyrrole, oxazole, thiazole, isooxazole, isothiazole, oxadiazole, thiadiazole, pyrazole, imidazole, triazole, tetrazole, indole, benzofuran, benzothiophene, benzooxazole, benzothiazole, benzooxadiazole, benzothiadiazole, benzopyrazole, benzimidazole, benzotriazole, triazolepyridine, triazolepyrimidine, coumarin.

The term "cyclo or polycyclic system" refers to a system containing one or more rings containing from 3 to 14 carbon atoms, optionally containing heteroatoms selected from nitrogen, oxygen, sulfur, silicon, selenium, phosphorous. Specific examples of a cyclo or polycyclic system are: thieno[3,2-b]thiophene, thiadiazole, benzothiophene, quinoxaline, pyridine.

The above process can be carried out according to the following scheme:

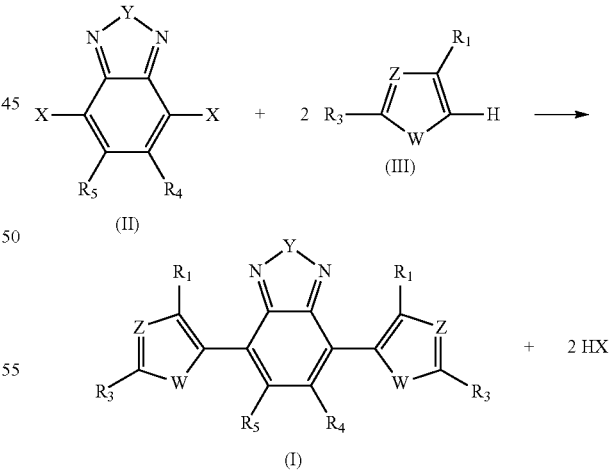

wherein X, Y, Z, W, $R_1$, $R_3$, $R_4$ and $R_5$, have the same meanings described above.

According to a preferred embodiment of the present invention, said disubstituted benzohetero[1,3]diazole compound having general formula (II) and said heteroaryl compound having general formula (III) can be used in molar ratios ranging from 1:2 to 1:20, preferably ranging from 1:4 to 1:12.

According to a further preferred embodiment of the present invention, said process relates to the preparation of a benzohetero[1,3]diazole compound disubstituted with heteroaryl groups having general formula (I) wherein:
W represents a sulfur atom, or an oxygen atom;
Y represents a sulfur atom, an oxygen atom, or an NR group wherein R represents a $C_1$-$C_{20}$ alkyl group, preferably an ethyl-hexyl group;
Z represents a nitrogen atom, or a $CR_2$ group wherein $R_2$ is a hydrogen atom, or a $CR_2$ group wherein $R_2$ and $R_3$ are bound to each other and form a saturated polycyclic system with 6 carbon atoms containing two sulfur atoms, preferably a thieno[3,2-b]thiophene;
$R_1$, $R_3$, $R_4$ and $R_5$, represent a hydrogen atom; or $R_1$, $R_4$ and $R_5$, represent a hydrogen atom and $R_3$ represents a —COR group wherein R is a $C_1$-$C_{20}$ alkyl group, preferably a methyl; or $R_1$, $R_2$, $R_4$ and $R_5$, represent a hydrogen atom and $R_3$ represents a heteroaryl group optionally substituted with a $C_1$-$C_{20}$ alkyl group, preferably 5-hexyl-thiophene.

According to a particularly preferred embodiment of the present invention, said process relates to the preparation of 4,7-di-2-thienyl-2,1,3-benzothiadiazole corresponding to a benzohetero[1,3]diazole compound disubstituted with heteroaryl groups having general formula (I) wherein W represents a sulfur atom, Y represents a sulfur atom, Z represents a $CR_2$ group and $R_1$, $R_2$, $R_3$, $R_4$ and $R_5$ represent a hydrogen atom, said process comprising reacting 4,7-dibromo-2,1,3-benzothiadiazole corresponding to a disubstituted benzohetero[1,3]diazole compound having general formula (II) wherein X represents a bromine atom, Y represents a sulfur atom and $R_3$ and $R_4$ represent a hydrogen atom, with a thiophene corresponding to a heteroaryl compound having general formula (III) wherein W represents a sulfur atom, Z represents a $CR_2$ group wherein $R_2$ represents a hydrogen atom and $R_1$ and $R_3$ represent a hydrogen atom.

According to a preferred embodiment of the present invention, said process can be carried out in the presence of at least one weak organic base.

According to a preferred embodiment of the present invention, said weak organic base can be selected, for example, from: carboxylates of alkaline metals (e.g., sodium, potassium, caesium) or alkaline-earth metals (e.g., magnesium, calcium) such as, for example, potassium acetate, sodium acetate, caesium acetate, magnesium acetate, calcium acetate, potassium propionate, sodium propionate, caesium propionate, magnesium propionate, calcium propionate, or mixtures thereof; carbonates of alkaline metals (e.g., lithium, sodium, potassium, caesium) or alkaline-earth metals (e.g., magnesium, calcium) such as, for example, lithium carbonate, potassium carbonate, sodium carbonate, caesium carbonate, magnesium carbonate, calcium carbonate, or mixtures thereof; bicarbonates of alkaline metals (e.g., lithium, sodium, potassium, caesium) or alkaline-earth metals (e.g., magnesium, calcium) such as, for example, lithium bicarbonate, potassium bicarbonate, sodium bicarbonate, caesium bicarbonate, magnesium bicarbonate, calcium bicarbonate, or mixtures thereof; or mixtures thereof. Said weak organic base is preferably potassium acetate.

According to a preferred embodiment of the present invention, said disubstituted benzohetero[1,3]diazole compound having general formula (II) and said weak organic base can be used in molar ratios ranging from 1:2.2 to 1:20, preferably ranging from 1:2.5 to 1:4.

According to a preferred embodiment of the present invention, said process can be carried out in the presence of at least one catalyst containing palladium.

According to a preferred embodiment of the present invention, said catalyst containing palladium can be selected from: palladium compounds in oxidation state (0) or (II) such as, for example, palladium(II) chloride [$PdCl_2$], palladium(II) acetate [$Pd(OAc)_2$], bis(dibenzylidene)palladium(0) [$Pd(dba)_2$ wherein dba=$C_6H_5CH$=$CHCOCH$=$CHC_6H_5$], bis(acetonitrile) palladium(II) chloride [$Pd(CH_3CN)_2Cl_2$], or mixtures thereof. Said catalyst containing palladium is preferably palladium(II) acetate [$Pd(OAc)_2$].

According to a preferred embodiment of the present invention, said disubstituted benzohetero[1,3]diazole compound having general formula (II), and said catalyst containing palladium can be used in molar ratios ranging from 100:0.1 to 100:3, preferably ranging from 100:0.4 e 100:2.

According to a preferred embodiment of the present invention, said disubstituted benzohetero[1,3]diazole compound having general formula (II) can be used at a molar concentration ranging from 0.1 M to 1 M, preferably ranging from 0.15 M to 0.5 M.

According to a preferred embodiment of the present invention, said process can be carried out in the presence of at least one dipolar aprotic organic solvent.

According to a preferred embodiment of the present invention, said dipolar aprotic organic solvent can be selected from: N,N-dimethylacetamide (DMAc), dimethylsulfoxide (DMSO), N-methylpyrrolidone (NMP), dimethylformamide (DMF), or mixtures thereof. Said dipolar aprotic organic solvent is preferably N,N-dimethylacetamide (DMAc).

According to a preferred embodiment of the present invention, said process can be carried out at a temperature ranging from 80° C. to 170° C., preferably ranging from 100° C. to 150° C.

According to a preferred embodiment of the present invention, said process can be carried out for a time ranging from 30 minutes to 24 hours, preferably ranging from 1 hour to 12 hours.

The disubstituted benzohetero[1,3]diazole compound having general formula (II) can be obtained according to processes known in the art, for example, by halogenation of the corresponding benzohetero[1,3]diazole compounds. Further details relating to said processes can be found, for example, in international patent application WO 2007/081991, or in "Journal of Heterocyclic Chemistry" (1970), Vol. 7, Issue 3, pages 629-633, in the article of Pilgram et al.

The heteroaryl compound having general formula (III) can be easily found on the market.

Some illustrative and non-limiting examples are provided for a better understanding of the present invention and for its practical embodiment.

EXAMPLE 1

Preparation of
4,7-di-2-thienyl-2,1,3-benzothiadiazole Having
Formula (a)

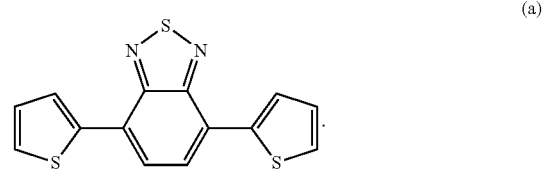 [SMILES: c1csc(-c2ccc(-c3cccs3)c3nsnc23)c1]

(a)

4,7-dibromo-2,1,3-benzothiadiazole (0.294 g, 1.0 mmoles), potassium acetate (0.295 g, 3.0 mmoles), N,N-dimethylacetamide (5 ml), thiophene (0.842 g, 10 mmoles) and palladium (II) acetate [Pd(OAc)$_2$] (1.2 mg, 0.005 mmoles), were charged into a 10 ml Pyrex glass reactor equipped with a screw stopper.

The reactor was placed in an oil bath preheated to 130° C. and left under vigorous stirring, for 4 hours. After cooling to room temperature (25° C.), the reaction mixture was put into a saturated solution of sodium chloride (25 ml) and extracted with ethyl acetate (3×ml). The organic phase obtained was dried on anhydrous sodium sulfate and evaporated. The residue obtained (brown solid) was purified by flash chromatography on silica gel using a mixture of n-heptane/ethyl acetate (1/1, vol/vol), as eluent, obtaining 240 mg of pure 4,7-di-2-thienyl-2,1,3-benzo-thiadiazole as a red solid (yield 80%).

Said 4,7-di-2-thienyl-2,1,3-benzothiadiazole was characterized by means of $^1$H-NMR (400 MHz, CDCl$_3$) obtaining the following spectrum: δ=8.07 (dd, J=3.8, 1.2 Hz, 2H), 7.80 (s, 2H), 7.42 (dd, J=5.1, 1.1 Hz, 2H), 7.18 (dd, J=5.1, 3.8 Hz, 2H).

Said 4,7-di-2-thienyl-2,1,3-benzothiadiazole was also characterized by means of MS mass analysis obtaining the following value: m/z: 301 (M$^+$).

EXAMPLE 2

Preparation of 4,7-bis-(5'-acetylthienyl)-2,1,3-benzo-thiadiazole Having Formula (b)

(b)

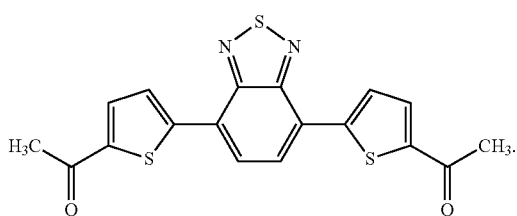

4,7-dibromo-2,1,3-benzothiadiazole (0.294 g, 1.0 mmoles), potassium acetate (0.295 g, 3.0 mmoles), N,N-dimethylacetamide (5 ml), 1-(thiophene-2-yl)ethanone (0.631 g, 5 mmoles) and palladium (II) acetate [Pd(OAc)$_2$] (1.2 mg, 0.005 mmoles), were charged into a ml Pyrex glass reactor equipped with a screw stopper.

The reactor was placed in an oil bath preheated to 120° C. and left under vigorous stirring for 18 hours. Operating subsequently as described in Example 1, 339 mg of pure 4,7-bis-(5'-acetylthienyl)-2,1,3-benzo-thiadiazole were obtained as a red solid (yield 88%).

Said 4,7-bis-(5'-acetylthienyl)-2,1,3-benzothia-diazole was characterized by means of $^1$H-NMR (400 MHz, CDCl$_3$) obtaining the following spectrum: δ=8.13 (d, J=4.0 Hz, 2H), 7.96 (s, 2H), 7.76 (d, J=4.0 Hz, 2H), 2.62 (s, 6H).

Said 4,7-bis-(5'-acetylthienyl)-2,1,3-benzothia-diazole was also characterized by means of MS mass analysis obtaining the following value: m/z: 384 (M$^+$).

EXAMPLE 3

Preparation of 4,7-bis-(5'-hexyl-2,2'-bithienyl)-2,1,3-benzothiadiazole Having Formula (c)

(c)

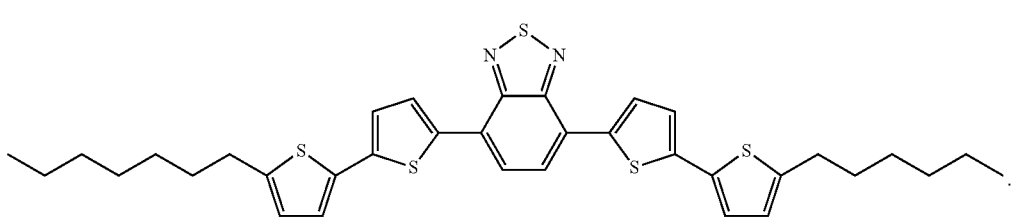

4,7-dibromo-2,1,3-benzothiadiazole (0.294 g, 1.0 mmoles), potassium acetate (0.295 g, 3.0 mmoles), N,N-dimethylacetamide (5 ml), 5-hexyl-2,2'-dithiophene (1.252 g, 5 mmoles) and palladium (II) acetate [Pd(OAc)$_2$] (1.2 mg, 0.005 mmoles), were charged into a 10 ml Pyrex glass reactor equipped with a screw stopper.

The reactor was placed in an oil bath preheated to 120° C. and left under vigorous stirring for 18 hours. Operating subsequently as described in Example 1, 512 mg of pure 4,7-bis-(5'-hexyl-2,2'-bithienyl)-2,1,3-benzothiadiazole were obtained as a red solid (yield 81%).

Said 4,7-bis-(5'-hexyl-2,2'-bithienyl)-2,1,3-benzo-thiadiazole was characterized by means of $^1$H-NMR (400 MHz, CDCl$_3$) obtaining the following spectrum: δ=8.03 (d, J=4.0 Hz, 2H), 7.83 (s, 2H), 7.19 (d, J=4.0 Hz, 2H), 7.11 (d, J=3.6 Hz, 2H), 6.73 (d, J=3.6 Hz, 2H), 2.82 (t, J=7.6 Hz, 4H), 1.73-1.69 (m, 4H), 1.42-1.39 (m, 4H), 1.35-1.31 (m, 8H), 0.82-0.73 (m, 6H).

Finally, said 4,7-bis-(5'-hexyl-2,2'-bithienyl)-2,1,3-benzothiadiazole was also characterized by means of MS mass analysis obtaining the following value: m/z: 632 (M$^+$).

EXAMPLE 4

Preparation of 4,7-bis-(thieno[3,2-b]thiophene-2-yl)-2,1,3-benzothiadiazole Having Formula (d)

(d)

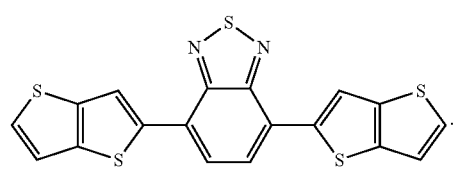

4,7-dibromo-2,1,3-benzothiadiazole (0.294 g, 1.0mmoles), potassium acetate (0.295 g, 3.0 mmoles), N,N-dimethylacetamide (5 ml), thienyl[3,2-b]thiophene (0.702 g, 5 mmoles) and palladium (II) acetate [Pd(OAc)$_2$] (1.2 mg, 0.005 mmoles), were charged into a 10 ml Pyrex glass reactor equipped with a screw stopper.

The reactor was placed in an oil bath preheated to 120° C. and left under vigorous stirring for 18 hours. Operating subsequently as described in Example 1, 251 mg of pure 4,7-bis-(thieno[3,2-b]thiophene-2-yl)-2,1,3-benzothiadiazole were obtained as a red solid (yield 61%).

Said 4,7-bis-(thieno[3,2-b]thiophene-2-yl)-2,1,3-benzothiadiazole was characterized by means of $^1$H-NMR (400 MHz, CDCl$_3$) obtaining the following spectrum: δ=8.49 (s, 2H), 7.87 (s, 2H), 7.45 (d, J=5.2 Hz, 2H), 7.31 (d, J=5.2 Hz, 2H).

Said 4,7-bis-(thieno[3,2-b]thiophene-2-yl)-2,1,3-benzothiadiazole was also characterized by means of MS mass analysis obtaining the following value: m/z: 412 (M$^+$)

EXAMPLE 5

Preparation of 4,7-di-(thiazol-5-yl)-2,1,3-benzothiadiazole Having Formula (e)

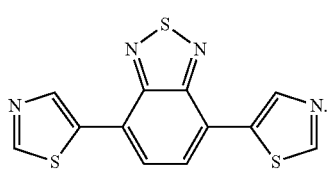

(e)

4,7-dibromo-2,1,3-benzothiadiazole (0.294 g, 1.0 mmoles), potassium acetate (0.295 g, 3.0 mmoles), N,N-dimethylacetamide (5 ml), thiazole (0.851 g, 5 mmoles) and palladium (II) acetate [Pd(OAc)$_2$] (1.2 mg, 0.005 mmoles), were charged into a 10 ml Pyrex glass reactor equipped with a screw stopper.

The reactor was placed in an oil bath preheated to 120° C. and left under vigorous stirring for 18 hours. Operating subsequently as described in Example 1, 194 mg of pure 4,7-di-(thiazol-5-yl)-2,1,3-benzothia-diazole were obtained as a red solid (yield 64%).

Said 4,7-di-(thiazol-5-yl)-2,1,3-benzothiadiazole was characterized by means of $^1$H-NMR (400 MHz, CDCl$_3$) obtaining the following spectrum: δ=9.01 (s, 2H), 8.92 (s, 2H), 7.98 (s, 2H).

Said 4,7-di-(thiazol-5-yl)-2,1,3-benzothiadiazole was also characterized by means of MS mass analysis obtaining the following value: m/z: 302 (M$^+$).

EXAMPLE 6

Preparation of 4,7-di-2-thienyl-2,1,3-benzooxadiazole Having Formula (f)

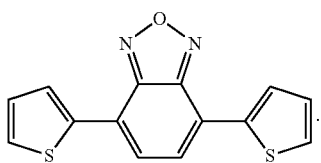

(f)

4,7-dibromo-2,1,3-benzothiadiazole (0.294 g, 1.0 mmoles), potassium acetate (0.295 g, 3.0 mmoles), N,N-dimethylacetamide (5 ml), thiophene (0.842 g, 5 mmoles) and palladium (II) acetate [Pd(OAc)$_2$] (1.2 mg, 0.005 mmoles), were charged into a 10 ml Pyrex glass reactor equipped with a screw stopper.

The reactor was placed in an oil bath preheated to 120° C. and left under vigorous stirring for 2 hours. Operating subsequently as described in Example 1, 233 mg of pure 4,7-di-2-thienyl-2,1,3-benzooxadiazole were obtained as a red solid (yield 82%).

Said 4,7-di-2-thienyl-2,1,3-benzooxadiazole was characterized by means of $^1$H-NMR (400 MHz, CDCl$_3$) obtaining the following spectrum: δ=8.11 (dd, J=3.6, 1.2 Hz, 2H), 7.61 (s, 2H), 7.44 (dd, J=5.2, 1.2 Hz, 2H), 7.20 (dd, J=5.2, 3.6 Hz, 2H).

Said 4,7-di-2-thienyl-2,1,3-benzooxadiazole was also characterized by means of MS mass analysis obtaining the following value: m/z: 284 (M$^+$).

EXAMPLE 7

Preparation of 2-(2-ethylhexyl)-4,7-di-(thiophene-2-yl)-2,1,3-benzotriazole Having formula (g)

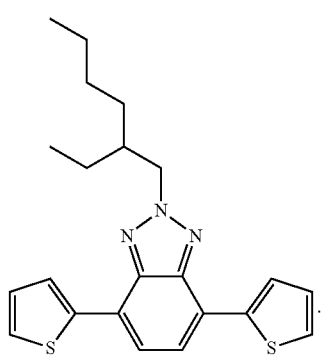

(g)

4,7-dibromo-(2-ethylhexyl)-1,3-benzothiadiazole (0.398 g, 1.0 mmoles), potassium acetate (0.295 g, 3.0 mmoles), N,N-dimethylacetamide (5 ml), thiophene (0.842 g, 5 mmoles) and palladium (II) acetate [Pd(OAc)$_2$] (1.2 mg, 0.005 mmoles), were charged into a 10 ml Pyrex glass reactor equipped with a screw stopper.

The reactor was placed in an oil bath preheated to 120° C. and left under vigorous stirring for 18 hours. Operating subsequently as described in Example 1, 265 mg of pure 2-(2-ethylhexyl)-4,7-di-(thiophene-2-yl)-2,1,3-benzotriazole were obtained as a red solid (yield 81%).

Said 2-(2-ethylhexyl)-4,7-di-(thiophene-2-yl)-2,1,3-benzotriazole was characterized by means of $^1$H-NMR (400 MHz, CDCl$_3$) obtaining the following spectrum: δ=8.10 (dd, J=3.6, 1.2 Hz, 2H), 7.63 (s, 2H), 7.38 (dd, J=5.2, 1.2 Hz, 2H), 7.19 (dd, J=5.2, 3.6 Hz, 2H), 4.75 (d, J=6.8 Hz, 2H), 2.25-2.32 (m, 1H), 1.48-1.36 (m, 6H), 1.34-1-28 (m, 2H), 1.08-0.98 (m, 3H), 0.93-0.89 (m, 3H).

Said 2-(2-ethylhexyl)-4,7-di-(thiophene-2-yl)-2,1,3-benzotriazole was also characterized by means of MS mass analysis obtaining the following value: m/z: 395 (M+).

EXAMPLE 8

Preparation of 4,7-di-2-furyl-2,1,3-benzothiadiazole Having Formula (h)

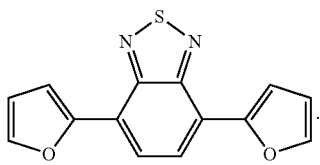

(h)

4,7-dibromo-(2-ethylhexyl)-1,3-benzothiadiazole (0.294 g, 1.0 mmoles), potassium acetate (0.295 g, 3.0 mmoles), N,N-dimethylacetamide (5 ml), furan (0.681 g, 10 mmoles) and palladium (II) acetate [Pd(OAc)$_2$] (1.2 mg, 0.005 mmoles), were charged into a 10 ml Pyrex glass reactor equipped with a screw stopper.

The reactor was placed in an oil bath preheated to 120° C. and left under vigorous stirring for 2 hours. Operating subsequently as described in Example 1, 212 mg of pure 4,7-di-2-furyl-2,1,3-benzothiadiazole were obtained as a red solid (yield 79%).

Said 4,7-di-2-furyl-2,1,3-benzothiadiazole was characterized by means of $^1$H-NMR (400 MHz, CDCl$_3$) obtaining the following spectrum: δ=8.02 (s, 2H), 7.67 (d, J=3.2 Hz, 2H), 7.58 (d, J=1.6 Hz, 2H), 6.62 (dd, J=3.2, 1.6 Hz, 2H).

Said 4,7-di-2-furyl-2,1,3-benzothiadiazole was also characterized by means of MS mass analysis obtaining the following value: m/z: 268 (M+).

The invention claimed is:

1. A process for the preparation of a benzohetero[1,3]diazole compound disubstituted with heteroaryl groups having general formula (I):

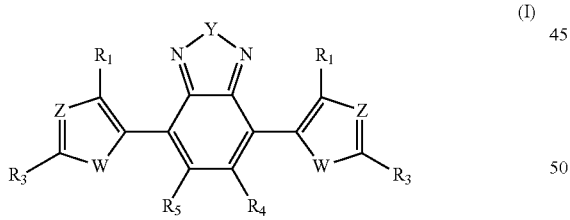

(I)

wherein:
W represents an oxygen atom; a sulfur atom; an NR group wherein R represents a hydrogen atom, or a linear or branched $C_1$-$C_{20}$ alkyl group;
Y represents a sulfur atom;
Z represents a nitrogen atom; or a CR$_2$ group wherein R$_2$ has the meanings reported below;
R$_1$ represents a hydrogen atom; a linear or branched $C_1$-$C_{20}$ alkyl group; a cycloalkyl group optionally substituted; an aryl group optionally substituted; a linear or branched $C_1$-$C_{20}$ alkoxyl group; a polyethyleneoxyl group R—O—[—CH$_2$—CH$_2$—O]$_n$— wherein R has the same meaning reported above and n is an integer ranging from 1 to 4; a —R'—OH group wherein R' represents a linear or branched $C_1$-$C_{20}$ alkylene group; a —R'—OR" group wherein R' has the same meanings reported above and R" represents a linear or branched $C_1$-$C_{20}$ alkyl group, or a polyethyleneoxyl group R—O—[—CH$_2$—CH$_2$—O]$_n$— wherein R has the same meaning reported above and n is an integer ranging from 1 to 4; a —COR group wherein R has the same meanings reported above; a —COOR group wherein R has the same meanings reported above; a —CHO group; a cyano (—CN) group;
R$_3$ represents a hydrogen atom; a linear or branched $C_1$-$C_{20}$ alkyl group; a cycloalkyl group optionally substituted; an aryl group optionally substituted; a heteroaryl group optionally substituted; a —CHO group; a —COR group wherein R has the same meanings reported above; a —COOR group wherein R has the same meanings reported above; a —CONR$_2$ group wherein R$_2$ has the same meanings reported below; a cyano (—CN) group;
R$_2$ represents a hydrogen atom; a linear or branched $C_1$-$C_{20}$ alkyl group; or, when R$_3$ is different from hydrogen, or when R$_1$=R$_2$, R$_2$ represents a linear or branched $C_1$-$C_{20}$ alkoxyl group;
or R$_1$ and R$_2$, can be optionally bound to each other so as to form, together with the carbon atoms to which they are bound, a cyclic or a polycyclic system containing from 3 to 14 carbon atoms, saturated, unsaturated, or aromatic, optionally containing one or more heteroatoms;
or R$_2$ and R$_3$, can be optionally bound to each other so as to form, together with the carbon atoms to which they are bound, a cyclic or a polycyclic system containing from 3 to 14 carbon atoms, saturated, unsaturated, or aromatic, optionally containing one or more heteroatoms;
or R$_4$ and R$_5$, the same as each other, represent a hydrogen atom; a linear or branched $C_1$-$C_{20}$ alkyl group; a linear or branched $C_1$-$C_{20}$ alkoxyl group; a —COOR group wherein R has the same meanings reported above; a cyano (—CN) group;
or R$_4$ and R$_5$, can be optionally bound to each other so as to form, together with the carbon atoms to which they are bound, a cyclic or a polycyclic system containing from 3 to 14 carbon atoms, saturated, unsaturated, or aromatic, optionally containing one or more heteroatoms;
said process comprising:
reacting at least one disubstituted benzohetero[1,3]diazole compound having general formula (II):

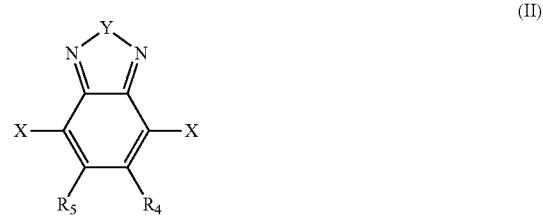

(II)

wherein X represents a halogen atom selected from chlorine, fluorine, bromine, iodine; Y, R$_4$ and R$_5$, have the same meanings described above;

with at least one heteroaryl compound having general formula (III):

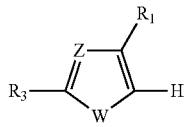

wherein W, Z, $R_1$ and $R_3$, have the same meanings described above.

2. The process according to claim 1, wherein said disubstituted benzohetero[1,3]diazole compound having general formula (II) and said heteroaryl compound having general formula (III) are used in molar ratios ranging from 1:2 to 1:20.

3. The process according to claim 2, wherein said disubstituted benzohetero[1,3]diazole compound having general formula (II) and said heteroaryl compound having general formula (III) are used in molar ratios ranging from 1:4 to 1:12.

4. The process according to claim 1, wherein said process relates to the preparation of a benzohetero[1,3]diazole compound disubstituted with heteroaryl groups having general formula (I) wherein:
W represents a sulfur atom, or an oxygen atom;
Y represents a sulfur atom;
Z represents a nitrogen atom, or a $CR_2$ group wherein $R_2$ is a hydrogen atom, or a $CR_2$ group wherein $R_2$ and $R_3$ are bound to each other and form a saturated polycyclic system with 6 carbon atoms containing two sulfur atoms;
$R_1$, $R_3$, $R_4$ and $R_5$, represent a hydrogen atom; or $R_1$, $R_4$ and $R_5$, represent a hydrogen atom and $R_3$ represents a —COR group wherein R is a $C_1$-$C_{20}$ alkyl group; or $R_1$, $R_2$, $R_4$ and $R_5$, represent a hydrogen atom and $R_3$ represents a heteroaryl group optionally substituted with a $C_1$-$C_{20}$ alkyl group.

5. The process according to claim 1, wherein said process relates to the preparation of 4,7-di-2-thienyl-2,1,3-benzothiadiazole corresponding to a benzohetero[1,3]diazole compound disubstituted with heteroaryl groups having general formula (I) wherein W represents a sulfur atom, Y represents a sulfur atom, Z represents a $CR_2$ group and $R_1$, $R_2$, $R_3$, $R_4$ and $R_5$ represent a hydrogen atom, said process comprising reacting 4,7-dibromo-2,1,3-benzothiadiazole corresponding to a disubstituted benzohetero[1,3]diazole compound having general formula (II) wherein X represents a bromine atom, Y represents a sulfur atom and $R_3$ and $R_4$ represent a hydrogen atom, with a thiophene corresponding to a heteroaryl compound having general formula (III) wherein W represents a sulfur atom, Z represents a $CR_2$ group wherein $R_2$ represents a hydrogen atom and $R_1$ and $R_3$ represent a hydrogen atom.

6. The process according to claim 1, wherein said process is carried out in the presence of at least one weak organic base.

7. The process according to claim 6, wherein said weak organic base is selected from: carboxylates of alkaline or alkaline-earth metals; carbonates of alkaline or alkaline-earth metals; bicarbonates of alkaline or alkaline-earth metals; or mixtures thereof.

8. The process according to claim 7, wherein said weak organic base is potassium acetate.

9. The process according to claim 1, wherein said disubstituted benzohetero[1,3]diazole compound having general formula (II) and said weak organic base are used in molar ratios ranging from 1:2.2 to 1:20.

10. The process according to claim 9, wherein said disubstituted benzohetero[1,3]diazole compound having general formula (II) and said weak organic base are used in molar ratios ranging from 1:2.5 to 1:4.

11. The process according to claim 1, wherein said process is carried out in the presence of at least one catalyst containing palladium.

12. The process according to claim 11, wherein said catalyst containing palladium is selected from palladium compounds in oxidation state (0) or (II), or mixtures thereof.

13. The process according to claim 12, wherein said catalyst containing palladium is palladium(II) acetate [Pd(OAc)$_2$].

14. The process according to claim 1, wherein said disubstituted benzohetero[1,3]diazole compound having general formula (II), and said catalyst containing palladium are used in molar ratios ranging from 100:0.1 to 100:3.

15. The process according to claim 14, wherein said disubstituted benzohetero[1,3]diazole compound having general formula (II), and said catalyst containing palladium are used in molar ratios ranging from 100:0.4 to 100:2.

16. The process according to claim 1, wherein said disubstituted benzohetero[1,3]diazole compound having general formula (II) is used at a molar concentration ranging from 0.1 M to 1 M.

17. The process according to claim 16, wherein said disubstituted benzohetero[1,3]diazole compound having general formula (II) is used at a molar concentration ranging from 0.15 M to 0.5 M.

18. The process according to claim 1, wherein said process is carried out in the presence of at least one dipolar aprotic organic solvent.

19. The process according to claim 18, wherein said dipolar aprotic organic solvent is selected from: N,N-dimethylacetamide (DMAc), dimethylsulfoxide (DMSO), N-methylpyrrolidone (NMP), dimethylformamide (DMF), or mixtures thereof.

20. The process according to claim 19, wherein said dipolar aprotic organic solvent is N,N-dimethylacetamide (DMAc).

21. The process according to claim 1, wherein said process is carried out at a temperature ranging from 80° C. to 170° C.

22. The process according to claim 21, wherein said process is carried out at a temperature ranging from 100° C. to 150° C.

23. The process according to claim 1, wherein said process is carried out for a time ranging from 30 minutes to 24 hours.

24. The process according to claim 1, wherein said process is carried out for a time ranging from 1 hour to 12 hours.

* * * * *